United States Patent
Gause et al.

(10) Patent No.: US 9,931,361 B2
(45) Date of Patent: Apr. 3, 2018

(54) TREATMENT TO PROMOTE WOUND HEALING

(71) Applicant: Rutgers, The State University of New Jersey, New Brunswick, NJ (US)

(72) Inventors: William C. Gause, Chester, NJ (US); Fei Chen, Denville, NJ (US); Zhugong Liu, Boyds, MD (US); Pankaj Mishra, Harrison, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 0 days.

(21) Appl. No.: 14/218,189

(22) Filed: Mar. 18, 2014

(65) Prior Publication Data

US 2015/0079134 A1 Mar. 19, 2015

Related U.S. Application Data (60) Provisional application No. 61/802,959, filed on Mar. 18, 2013.

(51) Int. Cl.
*A61K 35/62* (2006.01)
*A61K 39/00* (2006.01)

(52) U.S. Cl.
CPC .......... *A61K 35/62* (2013.01); *A61K 39/0003* (2013.01)

(58) Field of Classification Search
None
See application file for complete search history.

(56) References Cited

U.S. PATENT DOCUMENTS

| | | | | |
|---|---|---|---|---|
| 6,090,413 A | * | 7/2000 | Lee et al. | 424/520 |
| 2006/0030539 A1 | * | 2/2006 | Nick | A61K 31/522 514/44 R |
| 2008/0260784 A1 | * | 10/2008 | Mills | A61K 38/164 514/1.1 |

FOREIGN PATENT DOCUMENTS

WO  WO 2008144019 A2 * 11/2008 ............. A61K 38/42

OTHER PUBLICATIONS

Hewitson et al. 2009 (Helminth immunoregulation: The role of parasite secreted proteins in modulating host immunity; Molecular and Biochemical Parasitology 167:1-11.*

Eming et al. 2014 (Wound repair and regeneration: Mechanisms, signaling, and translation; Science Translational Medicine 6:265 1:16).*
Mehrabi et al. 2006 (Wound complications following kidney and liver transplantation; Clin Transplant 20 (Suppl 17):97-110).*
Gurtner et al. 2008 (Wound repair and regeneration; Nature 453(15):314-321).*
Guo et al. 2010 (Factors Affecting Wound Healing; Journal of Dental Research 89(3):219-229).*
Subbiahdoss et al. 2009 (Microbial biofilm growth vs. Tissue integration: "The race for the surface" Experimentally Studied; Acta Biomaterialia 5:1399-1404).*
Hewitson et al. 2009 (Helminth immunoregulation: The role of parasite secreted proteins in modulation host immunity; Molecular and Biochemical Parasitology 167: 1-11).*
Alonso and Fuchs, "Stem Cells in the the Skin: Waste Not, Wnt Not," Genes Dev., 2003, vol. 17, pp. 1189-1200.
Chigurupati, et al., "A Synthetic Uric Acid Analog Accelerates Cutaneous Wound Healing in Mice," PLoS One, 2010, vol. 5, p. e10044.
Gause, et al., "Type 2 Immunity and Wound Healing: Evolutionary Refinement of Adaptive Immunity by Helminths," Nature Reviews, 2013, vol. 13, pp. 607-614 (Abstract).
Jones et al., "In vivo measurement of neutrophil activity in experimental lung inflammation," Am J Respir Crit Care Med, Jun. 1994, vol. 149, No. 6, pp. 1635-1639 (Abstract).
Ojha, et al., "Assessment of wound-site redox environment and the significance of Rac2 in cutaneous healing," Free Radic Biol Med, Feb. 2008, vol. 44, No. 4, pp. 682-691.
Reiss, et al., "Matrix Metalloproteinase-9 Delays Wound Healing in a Murine Wound Model," Surgery, Feb. 2010, vol. 147, No. 2, pp. 295-302.
Syeda, et al., "Prostaglandin Transporter Modulates Wound Healing in Diabetes by Regulating Prostaglandin-Induced Angiogenesis," Am J Pathol, Jul. 2012, vol. 181, No. 1, pp. 334-346.
Wilgus et al., "Reduction of scar formation in full-thickness wounds with topical celecoxib treatment," Wound Repair, 2003, vol. 11, pp. 25-34 (Abstract).
Chen et al: "An Essential Role for TH2-Type Responses in Limiting Acute Tissue Damage During Experimental Helminth Infection", Nature Medicine, Feb. 2012, vol. 18, No. 2, pp. 260-267.

* cited by examiner

*Primary Examiner* — Mary Lyons
(74) *Attorney, Agent, or Firm* — Fox Rothschild LLP (57) ABSTRACT

The invention relates to a field of tissue repair and regeneration. More particularly, the invention relates to a composition for promoting cutaneous wound healing. In one embodiment, the composition is composed of one or more metazoan parasites or a mimic thereof sufficient to promote helminth-induced type-2 immune response. Preferably, the composition contains *N. brasiliensis* excretory/secretory antigen (NES) or an immune triggering portion thereof. The invention also relates to a method of accelerating wound healing in a subject in need of such treatment.

10 Claims, 2 Drawing Sheets

TREATMENT TO PROMOTE WOUND HEALING

CROSS-REFERENCE TO A RELATED APPLICATION

This application claims the benefit under 35 U.S.C. 119(e) of U.S. Provisional Application No. 61/802,959 filed on Mar. 18, 2013, the content of which is incorporated herein in its entirety.

STATEMENT OF GOVERNMENT LICENSE RIGHTS

The present invention was made with government support under grant number AI031678 awarded by the National Institutes of Health. The United States government may have certain rights in this invention.

FIELD OF THE INVENTION

The invention relates to a field of tissue repair and regeneration. More particularly, the invention relates to a composition for promoting cutaneous wound healing. In one embodiment, the composition is composed of one or more metazoan parasites or a mimic thereof sufficient to promote helminth-induced type-2 immune response. Preferably, the composition contains N. brasiliensis excretory/secretory antigen (NES) or an immune triggering portion thereof. The invention also relates to a method of accelerating wound healing in a subject in need of such treatment.

BACKGROUND

Vertebrates, including mammals, must be prepared for defense against two distinct types of infectious insult. In the first instance, rapidly replicating micro-organisms such as bacteria, viruses, protozoa or fungi have the potential to overcome host defenses by sheer numbers. In the second, the body's protective barriers are breached by physical trauma as occurs when helminths and other metazoan parasites enter, migrate or exit their host. Infection by metazoan parasites is ubiquitous and seriously compromises host fitness.

In humans, helminths not only cause overt morbidity but contribute to anaemia and impaired physical and cognitive development, which can result in poor school or work performance. The powerful selective force of macroparasite infection in mammals is illustrated by direct effects on host fecundity energy consumption and ability to survive the winter. This selection pressure has led to the evolution of a host protective response, which includes the rapid repair of tissues to tolerate the damage caused by these macroparasites as well as resistance mechanisms to reduce parasite burden.

The type 2 arm of the immune system is essential for helminth control. It evolved from a progenitor wound healing response largely as a consequence of the exposure to tissue damaging macroparasites. During this dynamic vertebrate:macroparasite coevolutionary process, important additional characteristics were incorporated that together contribute both to increased tolerance, through enhanced wound healing, and to parasite resistance. In the course of evolution type 2 cytokines may have come to direct wound repair machinery not only towards tissue repair and reconstruction but also to containment, destruction, and expulsion of helminths and other macroparasites. For example, reparative cells or pathways may promote rapid encapsulation or efficient expulsion through the excess production of collagen or mucus, respectively. Thus, under the umbrella of type 2 immunity both wound repair and anti-worm effector pathways have evolved in tandem to mediate host protective helminth responses. Although type 2 immunity may include responses to a broad range of insults, it is the ability of helminth parasites to compromise host fitness that is likely to have driven the evolution of Th2 cells to control and direct the innate type 2 response towards reducing parasite numbers and more rapidly repairing the damage they inflict as they aggressively migrate through host tissues. This evolutionary view also encompasses the counter-regulatory nature of type 2 immunity, because a type 1 anti-microbial response directed at a large migrating worm would cause serious collateral damage and would need to be actively avoided and because effective wound repair requires suppression of inflammation to proceed. In other words, effective wound repair requires both the direct reconstruction of the injured tissue and suppression of pro-inflammatory responses.

In view of the foregoing, a solution which overcomes the above-described inadequacies and shortcomings in current wound repair techniques is desired. In particular, it would be desirable to develop a method that utilizes aspects of the type 2 immune elicited by helminth to promote tissue repair and wound healing.

SUMMARY OF THE INVENTION

Having recognized the shortcomings of the prior art, as one embodiment, a novel wound healing composition is provided having one or more helminthic parasite preparations, preferably live, or an active mimic thereof. The helminthic parasite preparation can be a whole parasite, a parasite extract, parasite eggs, parasite egg extract, parasite larvae, parasite larvae extract, parasite cercariae and/or parasite cercariae extract. The wound can be acute or chronic inflicted on skin tissue and/or on lung tissue. The composition can also contain a pharmaceutically acceptable carrier.

In some embodiments of the invention, the helminthic parasite is a nematode, and may be selected from *Nippostrongylus brasiliensis, Ascaris lumbricoides, Enterobuis vermicularis, Trichuris trichiura, Ancylostroma duodenale, Necator americanus, Strongyloides stercoralis,* and *Trichinella spiralis*. In other embodiments, the helminthic parasite is a platyhelminth selected from the group consisting of trematodes and cestodes, such as *Fasciolopsis, Echinostoma* and *Heterophyes* species, *Clonorchis sinensis, Oplishorchis viverrini, Opisthorchis felineus, Fasciola hepatica, Schistosoma* species, *Diphyllobothrium* species, *Taenia saginata, Taenia solium* and *Hymenolepsis nana*. In yet other embodiments, the helminthic parasites are selected from the group consisting of *Trichuris muris, Trichinella spiralis, Nippostronglylus prasiliensis, Heligmonsomoides polygyrus, Hymenolepsis nanan, Angiostrongylus* species, *Trichuris suis, Ascaris suum, Trichuris vulpis, Toxocara* species and *Pseudoterranova* species. In still other embodiments, the helminthic parasite is selected from the group consisting of filarial parasites and lung flukes. Preferably, the helminthic parasite is *Nippostrongylus brasiliensis* (Nh) and the helminthic parasite preparation contains Nb excretory/secretory antigen (NES) or an immune triggering portion thereof.

The disclosed compositions have particular application in the topical administration of active compounds for a local effect. As such, the composition may be in any form suitable for topical application to the skin. Suitable forms include sprayable liquids; gels; liquids that may be applied using a roll-on device; lacquers; and sustained release matrices of transdermal delivery devices such as patches. Localized subcutaneous injection of active compounds may also be used as a method of treatment.

The present invention is also directed to a method of wound healing or accelerating wound healing by administering to a wounded/damaged area of a patient in need of such treatment one or more helminthic parasite preparations, preferably live, or an active mimic thereof in the amount sufficient to promote or accelerate wound healing. Preferably, the helminthic parasite preparation contains *N. brasiliensis* excretory/secretory antigen or an immune triggering portion thereof (NES product). In some embodiments, the NES product can be administered before the subject is wounded.

In further embodiments, the present invention is directed to a method of treating an acute lung injury by administering to a patient in need of treatment one or more helminthic parasite preparations, preferably live, or an active mimic thereof, where the NES product is being preferred.

The present objectives, features and advantages will be apparent from the following detailed description of the invention, which is to be read in conjunction with the accompanying drawings. The scope of the invention will be pointed out in the claims. The following drawings, taken in conjunction with the subsequent description, are presented to enable one of ordinary skill in the art to make and use the invention and to incorporate it in the context of particular applications.

DETAILED DESCRIPTION OF THE INVENTION

In one embodiment, a novel method of treating wounds and/or accelerating wound healing is described. The method generally relies on administering to a wounded/damaged area of a patient in need of such treatment a composition containing one or more helminthic parasite preparations. Without being bound by theory, it is believed that type-2 immune responses to one or more members of the helminthic parasite preparation correlate with wound repair and its anti-inflammatory activity, which is directly connected to wound healing and prevention of autoimmune and allergic disease. In one embodiment, the helminthic parasite preparation contains a helminthic parasite, which can be live in some embodiments, in the amount sufficient to promote or accelerate wound healing.

Figure 1:
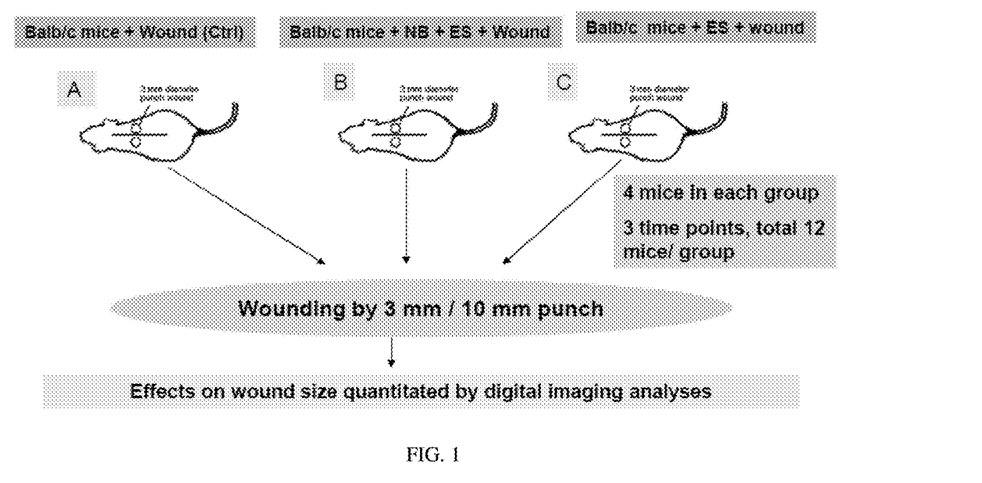
FIG. 1 is a diagram showing an exemplary treatment protocol with live Nb parasite and its derived NES product: (A) Control; (B) Nb+NES; (C) NES only.
Figure 2A:
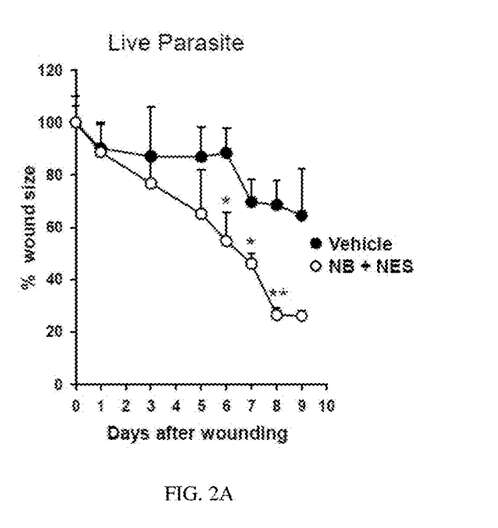
FIG. 2A is a plot of wound healing or closure (%) as a function of time based on administration of live Nb parasite together with Nb excretory/secretory (NES) product (open circles). Biopsy punch and wound healing was assessed by taking digital photographs of wounds at different time points. Wound closure was analyzed by calculating the wound area (pixels2) individually using digital imaging analysis software (Zeiss Axiovision 4.8.1). Student T test. * $p<0.05$ and ** $p<0.01$. The data confirms that the administration of live parasite together with ES product enhances tissue biopsy wound closure.
Figure 2B:
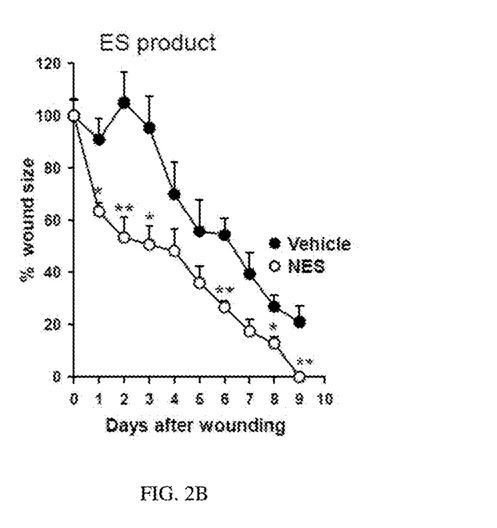
FIG. 2B is a plot of wound healing or closure (%) as a function of time based on administration of Nb excretory/secretory (NES) product (open circles). (* $p<0.05$ and ** $p<0.01$). The data confirms that the administration of the NES product enhances tissue biopsy wound closure.

The response needs to develop rapidly to enhance repair of damaged vital organs and to limit entry and promote expulsion of macroparasites in sensitized individuals at the earliest stages of infection. Rapid tissue repair is also vital to survival as it would prevent invasion of bacteria and other pathogenic organisms that could rapidly lead to sepsis. The response has multiple components with individual effector mechanisms tailored to enhance protective immunity against specific species of helminths and other macroparasites. In some embodiments of the invention, the helminthic parasite is a nematode, and may be selected form the group such as *Nippostrongylus brasiliensis, Ascaris lumbricoides, Enterobuis vermicularis, Trichuris trichiura, Ancylostroma duodenale, Necator americanus, Strongyloides stercoralis*, and *Trichinella spiralis*. In other embodiments, the helminthic parasite is a platyhelminth, and may be selected from the group consisting of trematodes and cestodes, such as *Fasciolopsis, Echinostoma* and *Heterophyes* species, *Clonorchis sinensis, Opisthorchis viverrini, Opisthorchis felineus, Fasciola hepatica, Schistosoma* species, *Diphyllobothrium* species, *Taenia saginata, Taenia solium* and *Hymenolepsis nana*. In yet other embodiments, the helminthic parasites are selected from the group consisting of *Trichuris muris, Trichinella spiralis, Nippostronglylus prasiliensis, Heligmonsomoides polygyrus, Hymenolepsis nanan, Angiostrongylus* species, *Trichuris suis, Ascaris suum, Trichuris vulpis, Toxocara* species and *Pseudoterranova* species. In still other embodiments, the helminthic parasite is selected from the group consisting of filarial parasites and lung flukes. Preferably, the helminthic parasite is *Nippostrongylus brasiliensis* (Nb) and the helminthic parasite preparation contains Nb excretory/secretory antigen (NES) or an immune triggering portion thereof. In one exemplary embodiment, a significant acceleration of wound healing is observed upon administration of Nb+ES compared to control groups (not administered Nb+ES) as illustrated in FIGS. 2A-2B).

Vertebrate/helminth coevolution plays a critical role in shaping a progenitor innate wound healing response into a host protective innate and adaptive type 2 response directed towards metazoan parasites. Components of the response may also be triggered by enzymes, particulates, and certain toxins, many of which mimic components or characteristics of helminths and other macroparasites and each of which elicit type-2 immunity in part through tissue damage. In one embodiment, the helminthic parasite preparation of present invention contains a whole parasite, a parasite extract, parasite eggs, parasite egg extract, parasite larvae, parasite larvae extract, parasite cercariae and/or parasite cercariae extract. In another embodiment, the helminthic parasite preparation contains excretory/secretory (ES) antigen of the helminthic parasite or an immune triggering portion thereof.

Tissue Damage and Initiation of Type 2 Responses

Although helminth molecules with direct Th2 inducing capacity exist, the large size of the parasite and the consequent tissue damage that occurs during invasion may well be more important. This is supported by studies showing that helminth invasion associated with tissue damage triggers the release of several epithelium-derived alarmins that can initiate type 2 immunity. One of the first such alarmins shown to play an important role in helminth-induced type 2 immunity was TSLP, with a recent study suggesting that TSLP directs type 2 immunity by eliciting a population of functionally distinct IL-4-producing basophils. Additional studies have suggested that the role of TSLP in eliciting type 2 immunity varies markedly with different helminthes, with at least some parasites bypassing the need for TSLP by directly suppressing the key type-1-inducing cytokine IL-12. In these cases, the Th2 response appears to emerge as a default response or may rely on other alarmins. IL-1R4 (T1/ST2) and its ligand IL-33, an alarmin released from the nucleus of necrotic epithelial and endothelial cells and fibroblasts, has also been shown to initiate type 2 responses. A similar role has been identified for the IL-17 family cytokine IL-25 (LL-17E). Thus multiple alarmins released by damaged epithelial cells are involved in the initiation of protective type-2 responses during macroparasite infection, with the relative importance of each mediator dictated by the pathogen and its mode of entry into the definitive host.

Strong support for the importance of injury in Type 2 induction comes from evidence that innocuous antigens, when exposed to the immune system in the context of cutaneous tissue damage, can trigger potent type 2 responses in part mediated by γδ T cells. In this case, type 2 immunity is activated by large inert particulate structures that cause direct cell and tissue damage, likely resulting in the release of alarmins and other cell-intrinsic danger-associated molecular patterns (DAMPs). For example, inert silica and titanium microparticles trigger innate type 2 responses and have been used as adjuvants to promote adaptive type 2 immunity. They induce type 2 responses through TLR4- and Myd88-independent pathways, thereby excluding the possibility of contaminating endotoxin or other PAMPs, which at low doses could stimulate type 2 responses. Alum may exploit a similar pathway, as its type 2 adjuvant activity at least partly results from uric acid crystals released from damaged tissues that drive type 2 immunity through inflammasome-independent pathways. In an asthma model, ATP, presumably released by damaged cells, binds P2 purinergic receptors that trigger the release of the alarmin, IL-33, in the lung resulting in type 2 immunity. Critically, no single cellular DAMP has been shown to be essential for the development of helminth-induced responses, suggesting a range of redundant pathways are involved in sensing helminth-induced danger. Indeed, multiple causes of tissue damage, including helminth derived proteases and insect venoms, contribute to the activation of type 2 responses.

Tissue stress and damage, in the absence of strong TLR signaling, may be a particularly potent combination for stimulating type 2 immunity. As such DAMPS, and the alarmins they elicit, may be the critical factors driving type 2 responses, with individual helminth excretory/secretory products in part contributing to the polarization of the response by conditioning dendritic cells to suppress TLR signals and the associated protein machinery required to prime Th1 cells. When alarmins are released during parasite induced tissue damage, an important part of their programming is to quickly induce the recruitment of type 2 innate lymphocytes (ILC2s), that secrete large quantities of IL-5 and IL-13, which then activate anti-parasite effector responses and initiate wound healing. These cells, along with multipotent progenitor type 2 cells, eosinophils, mast cells, and basophils, are rapidly recruited to the site of injury and serve as important innate sources of type-2 cytokines. Eosinophils and basophils in particular are important producers of IL-4, which further amplifies and instructs both innate and adaptive arms of type-2 immunity.

After initiation of the adaptive type 2 immune response, effector memory T cells, which rapidly secrete cytokines at high levels, and the production of IgE and IgG by B cells, can augment resistance to many helminthes. Shortly after infection many of these parasites migrate through tissues, such as the lung, where they are more actively targeted by immune cells, prior to their entry into the lumen of the small intestine Fcs receptors expressed on mast cells bind parasite specific IgE, and subsequent crosslinking by helminth Ag triggers degranulation and release of mediators that in some cases contribute to parasite expulsion, as has been suggested in the response to *Trichinella spiralis*. IgE-mediated rapid degranulation of mast cells may also be of importance against other macroparasites, such as ticks, as localized tissue edema may impede invasion. Because IgE receptors are found on cells specifically associated with repair, IgE may also accelerate or augment repair associated with a particular nematode, although this has not yet been investigated. Thus, a very rapid and sometimes complex immune response is needed to induce expulsion or killing and repair the damage caused by these large macroparasites.

Evidence Type 2 Immunity Instructs Tissue Repair

There is a direct role for the type 2 immune response in wound healing through both control of inflammation and through production of mediators that directly enhance the tissue repair process (Gause W. C. et al. *Nature Reviews* 2013, 13, 607-614; incorporated herein by reference in its entirety).

Effective wound repair requires both the direct reconstruction of the injured tissue and suppression of pro-inflammatory responses. Virtually all the cell types associated with immunity to helminth infections have been implicated in wound healing. These include T cells, eosinophils, alternatively-activated macrophages (AAMs), and ILC-2 cells, each of which also have demonstrated roles in worm expulsion or killing. Th2 cytokines, including IL-4, IL-5, and IL-13, mediate eosinophil activation and recruitment. These granulocytes store a variety of preformed mediators in intracellular granules, including cytokines, growth factors, matrix metalloproteinases (MMPs), cationic proteins and lipid mediators that can mediate wound healing, tissue remodelling, and myofibroblast differentiation. The differentiation of AAMs is largely dependent on the Th2 cytokines IL-4 and IL-13 and they characteristically produce high levels of RELM-α, Arginase 1 (Arg.1), Ym-1, and Insulin-like growth factor-1 (IGF-1), MMPs, growth factors, e.g. platelet-derived growth factor (PDGF), TREM-2 and TGF-β, which are all tightly associated with the wound healing response. A number of studies have shown marked increases in these same mediators during helminth infection, suggesting they may contribute to control of parasite induced tissue damage.

In the experimental model of schistosomiasis, the type 2 response plays an important host protective role during infection by inducing granulomas that sequester tissue-damaging toxins released by parasite eggs. If the Th2 response is impaired, infected animals develop defective granulomas and succumb quickly to the infection because they develop uncontrolled type-1/type-17 inflammatory reactions in the liver and intestine. More recently, specific blockade of Arg1 in *S. mansoni*-infected mice caused increased egg-associated intestinal tissue damage, hemorrhaging and disruption and leakage of the mucosal barrier, all of which were dependent on signaling through IL-12/IL-23p40. Thus, in this system Arg1 production by AAMs controls harmful inflammation associated with a type 1 response, which as a result contributes to tissue repair and maintenance of the mucosal barrier. In another model, infection with the nematode parasite *N. brasiliensis* triggers acute pulmonary hemorrhaging, as parasites traffic through the lung en route to the intestine. Recent studies indicate that physical damage caused by these migrating parasites and by IL-17 driven neutrophil inflammation cause extensive pulmonary tissue damage and hemorrhaging. The type 2 response, which develops shortly thereafter, markedly reduced the hemorrhaging and inflammation through IL-4Ralpha-dependent mechanisms. Macrophages showed high expression of insulin-like growth factor (IGF-1), which has also recently been shown to be elevated through the IL-4Ralpha in nematode-elicited macrophages and has been linked to tissue regeneration, collagen synthesis and fibroblast activation. Intriguingly, in the helminth lung model, IGF-1 is essential for the enhanced acute wound healing type 2 response. In another recent study, resident ILC-2 cells were shown to produce multiple genes associated with wound healing including the epidermal growth factor receptor ligand, amphiregulin. Depletion of ILC-2 cells in Influenza A infected mice compromised lung epithelial barrier integrity; however, barrier function was restored when amphiregulin was administered. Thus components of the innate type 2 immune response may be utilized during viral infection to mediate tissue repair. Intriguingly, amphiregulin is also produced by mast cells following Fc□RI signaling, raising a potential link between the IgE response and wound repair. Taken together, these recent studies have revealed several mechanisms through which the type 2 immune response promotes wound healing. These findings also indicate the importance of a rapidly developing type 2 response, even after a first exposure to helminthes, to mitigate the tissue damage caused as these large multicellular parasites migrate through different tissues.

In the *N. brasiliensis* lung model AAMs also engulf RBCs, which is consistent with other studies that have implicated AAMs in the phagocytosis and clearance of neutrophils. Although recent in vitro studies suggest AAMs may have impaired phagocytosis, these in vivo studies suggest they retain this important wound healing capability, at least in the context of helminth infection. Although some studies have suggested that IL-10 secreting macrophages also play an important protective role in the immune response to helminthes by suppressing inflammation, more recent studies have suggested that IL-10 is primarily produced by CD4+ T cells rather than macrophages. RNAseq analysis of macrophages during filarial nematode infection demonstrated a clear absence of IL-10 in AAMs, suggesting that in the absence of additional signals, such as TLR ligands or type 1 interferons, helminth induced AAMs do not secrete significant quantities of IL-10. These findings are consistent with the recently proposed wound healing macrophage phenotype and indicate that the majority of macrophages elicited during helminth infection may be distinct from inflammatory and regulatory macrophages that secrete IL-10. Taken together, these recent studies demonstrate that the type 2 response mediates tissue repair by both limiting inflammation and by directly activating mediators that then facilitate wound healing. As helminthes migrate through vital tissues, sometimes causing extensive tissue damage, the potent wound healing mechanisms induced by the type 2 immune response thereby enhance tolerance to these large multicellular organisms.

Protection Against Allergy and Autoimmune Disease—Helminths as Endogenous Regulators Suppression of inflammation is an integral part of type 2 immunity, not only important in wound healing but also in downregulating harmful inflammatory responses that by themselves can cause disease. The intense selection pressure that occurred during helminth/vertebrate coevolution has likely shaped the mammalian immune response and the presence of parasites may now be needed for optimal immune function and homeostasis in some tissues. Indeed, the marked reduction in helminth infections in industrialized countries has been causally linked to the rapid rise in the incidence of many inflammatory diseases due to a loss of associated immune regulatory components. Consistent with this model, a number of inflammatory diseases, including inflammatory bowel disease and type 1 diabetes (T1D), are markedly reduced in severity in several experimental models of helminth infection. Consequently, both helminth-derived products and live helminths are being evaluated as possible therapies for a variety of autoimmune and inflammatory diseases. However, thus far live infections appear superior, perhaps a consequence of their potent adjuvant activity due to direct tissue damage and release of alarmins, as discussed earlier.

The regulatory mechanisms induced by live helminth infections include both innate and adaptive components. Macrophages, Th2 cells, T reg cells, dendritic cells and NK T cells secreting various anti-inflammatory mediators, including IL-4, IL-10, and TGF-beta, have all been implicated in the downregulation of harmful type 1 inflammation during helminth infection. Although these mechanisms often collaborate to suppress tissue damaging inflammation, recent studies have suggested that IL-10 and TGF-beta operate independently of conventional Th2 cells and FOXP3-expressing Tregs, at least in terms of controlling inflammation and diabetes in nonobese diabetic (NOD) mice. Therefore, in future studies multiple potentially redundant regulatory pathways may need to be simultaneously blocked to elucidate their role in controlling type 1 driven inflammatory diseases.

The type 2 cytokine response thus maintains host fitness during helminth infection by downregulating inflammation, promoting wound healing, and reducing parasite numbers. However, helminth infection is typically chronic with persistent production of type 2 cytokines. If Type 2 immunity itself is not appropriately regulated, it can become pathogenic and contribute to the development of lethal fibrotic pathology, which results from overzealous or persistent wound healing responses. This is the situation in chronic schistosome infections, in which the type 2 cytokine response was identified as the critical driver of lethal hepatic fibrosis. In schistosomiasis, hepatic fibrosis contributes to the development of portal hypertension, triggering the formation of gastric and esophageal varices that are prone to rupture. Thus, development of fibrosis and portal hypertension are believed to be the major causes of morbidity and mortality in chronic schistosomiasis. While IL-4 was identified as the principle inducer of the protective type 2 response during acute *S. mansoni* infection, IL-13 was identified as the key driver of hepatic fibrosis in chronically infected mice. In mice, the progression of hepatic fibrosis in schistosomiasis correlates with the intensity of the IL-13 response, and immunologic interventions that selectively impair IL-13 activity have been shown to reduce collagen deposition and significantly improve survival as long as IL-4 production is preserved. Thus, type-2 cytokines exhibit both protective and pathogenic activity in chronic helminth infections, with each outcome being directly linked with either beneficial or aberrant wound healing responses.

The need to prevent the consequences of uncontrolled type 2 responses may in part explain the counter-intuitive observation that helminth infection can even attenuate harmful type 2 responses associated with allergy in experimental models. This is consistent with epidemiological observations suggesting the incidence of allergy is reduced in helminth-infected individuals. The marked influence of helminth infection on the development of allergic responses is consistent with a model where the immune system exhibits dysregulated responses, i.e. allergy, in the absence of chronic parasite infections. It is not consistent with alternative models suggesting that allergic responses may be beneficial in providing adverse responses to potentially noxious substances. This immune suppressive effect of helminth infection may be a consequence of the long-term relationship between host and parasite resulting in evasion mechanisms that enhance parasite survival through impaired type 2 immunity but also protect the host from damage caused by overzealous repair. IL-10, which can be produced by T effector, FOXP3+ T reg, and Tr1 cells, and also various innate populations after helminth infection, may be a particularly potent regulator of harmful type 2 immune responses. Other potent candidate negative regulators are Arginase-1, RELMα, and the IL-13 decoy receptor, each of which is produced by AAMacs, and is capable of downregulating type 2 responses. Some of these intrinsic and extrinsic regulatory components that control type 2 immunity, may be preferentially activated during helminth infection, in contrast to the immune response to allergens, providing a possible explanation for the severe type 2 inflammation associated with allergies. If so, it will be important in future studies to elucidate the mechanisms that preferentially trigger IL-10 and other regulatory molecules during the type 2 immune response to helminths as they may be harnessed for the development of future immunotherapies.

The wound can be acute or chronic, inflicted, in some embodiments, on skin tissue and, in other embodiments, on lung tissue. Effective dosages and schedules for administering the compositions may be determined empirically, and making such determinations is within the skill in the art. The dosage ranges for the administration of the compositions are those large enough to produce the desired effect in which the wound healing is effected. The dosage should not be so large as to cause adverse side effects, such as unwanted cross-reactions, anaphylactic reactions, and the like. Generally, the dosage will vary age, sex, weight and general condition of the subject, the severity of the wound being treated, the type of wound, the selected preparation (e.g., live parasite, eggs, larvae, antigen, etc.), the patient's immune state, its route of administration or whether other drugs are included in the regimen, and can be determined by one of skill in the art. The dosage can be adjusted by the individual doctor in the event of any counterindications. Dosage can vary, and can be administered in one or more dose administrations daily, for one or several days. Guidance can be found in the literature for appropriate dosages for given classes of pharmaceutical products. The range of dosage largely depends on the application of the compositions herein, severity of condition, and its route of administration.

However, in many instances the compositions would be formulated in such a way as to ensure that sufficient amount of the helminthic parasite preparation present in the composition to elicit Type-2 immunity after direct application of the composition to the skin. It is even envisaged that there be a range of preferred helminthic parasite preparation to give a pre-planned dosage rate over a defined period.

Following administration of a disclosed composition for promoting wound healing, the efficacy of the therapeutic composition can be assessed in various ways well known to the skilled practitioner. For instance, one of ordinary skill in the art will understand that a composition disclosed herein is efficacious in promoting wound healing in a subject by observing that the composition can reduce scar tissue formation, reduce fibrotic tissue formation, improve tissue regeneration, or reduce inflammation in the subject following tissue injury. Methods for measuring these criteria are known in the art and discussed herein.

In some embodiments, the composition further contains a pharmaceutically acceptable carrier or excipient suitable for use with humans and/or animals without undue adverse side effects (such as toxicity, irritation, and allergic response) commensurate with a reasonable benefit/risk ratio. The carrier would naturally be selected to minimize any degradation of the helminthic parasite preparation and to minimize any adverse side effects in the subject, as would be well known to one of skill in the art. Examples of pharmaceutically acceptable carriers include those selected from the group consisting of water, polyhydric alcohols including alkylene gycols, (particularly propylene glycol) and glycerol; alcohols such as ethanol and isopropanol; polyalkylene glycols such as polyethylene glycol; other ointment bases such as petroleum jelly, lanolin, dimethylformamide, ethylene glycol, tetrahydrofurfuryl alcohol, cyclohexane, cyclohexanone, acetone, ethylether, N-dodecylazocyclo-heptan-2-one, methyldecylsulfoxide, dimethylacetamide and diethylfoluamide; and mixtures thereof.

It should be appreciated that the above list is not exclusive as the present invention also encompasses the use of pharmaceutically acceptable carriers other than those specifically mentioned. In some embodiments, the composition may further contain thickeners, diluents, buffers, preservatives, surface active agents and the like in addition to the pharmaceutically acceptable carriers and the helminthic parasite preparation.

The herein provided composition can further comprise any known or newly discovered substance that can be administered to a wound, tissue injury, or site of inflammation that include antimicrobial agents, antiinflammatory agents, anesthetics, and the like. For example, the provided composition can further comprise one or more of classes of antibiotics (e.g. Aminoglycosides, Cephalosporins, Chloramphenicol, Clindamycin, Erythromycins, Fluoroquinolones, Macrolides, Azolides, Metronidazole, Penicillin's, Tetracycline's, Trimethoprim-sulfamethoxazole, Vancomycin), steroids (e.g. Andranes (e.g. Testosterone), Cholestanes (e.g. Cholesterol), Cholic acids (e.g. Cholic acid), Corticosteroids (e.g. Dexamethasone), Estraenes (e.g. Estradiol), Pregnanes (e.g. Progesterone), narcotic and non-narcotic analgesics (e.g. Morphine, Codeine, Heroin, Hydromorphone, Levorphanol, Meperidine, Methadone, Oxydone, Propoxyphene, Fentanyl, Methadone, Naloxone, Buprenorphine, Butorphanol, Nalbuphine, Pentazocine), chemotherapy (e.g. anti-cancer drugs such as but not limited to Altretamine, Asparaginase, Bleomycin, Busulfan, Carboplatin, Carrnustine, Chlorambucil, Cisplatin, Cladribine, Cyclophosphamide, Cytarabine, Dacarbazine, Diethylstilbesterol, Ethinyl estradiol, Etoposide, Floxuridine, Fludarabine, Fluorouracil, Flutamide, Goserelin, Hydroxyurea, Idarubicin, Ifosfamide, Leuprolide, Levamisole, Lomustine, Mechlorethamine, Medroxyprogesterone, Megestrol, Melphalan, Mercaptopurine, Methotrexate, Mitomycin, Mitotane, Mitoxantrone, Paclitaxel, pentastatin, Pipobroman, Plicamycin, Prednisone, Procarbazine, Streptozocin, Tamoxifen, Teniposide, Vinblastine, Vincristine), anti-inflammatory agents (e.g. Alclofenac; Alclometasone Dipropionate; Algestone Acetonide; alpha Amylase; Amcinafal; Amcinafide; Amfenac Sodium; Amiprilose Hydrochloride; Anakinra; Anirolac; Anitrazafen; Apazone; Balsalazide Disodium; Bendazac; Benoxaprofen; Benzydamine Hydrochloride; Bromelains; Broperamole; Budesonide; Carprofen; Cicloprofen; Cintazone; Cliprofen; Clobetasol Propionate; Clobetasone Butyrate; Clopirac; Cloticasone Propionate; Cormethasone Acetate; Cortodoxone; Decanoate; Deflazacort; Delatestryl; Depo-Testosterone; Desonide; Desoximetasone; Dexamethasone Dipropionate; Diclofenac Potassium; Diclofenac Sodium; Diflorasone Diacetate; Diflumidone Sodium; Diflunisal; Difluprednate; Diftalone; Dimethyl Sulfoxide; Drocinonide; Endrysone; Enlimomab; Enolicam Sodium; Epirizole; Etodolac; Etofenamate; Felbinac; Fenamole; Fenbufen; Fenclofenac; Fenclorac; Fendosal; Fenpipalone; Fentiazac; Flazalone; Fluazacort; Flufenamic Acid; Flumizole; Flunisolide Acetate; Flunixin; Flunixin Meglumine; Fluocortin Butyl; Fluorometholone Acetate; Fluquazone; Flurbiprofen; Fluretofen; Fluticasone Propionate; Furaprofen; Furobufen; Halcinonide; Halobetasol Propionate; Halopredone Acetate; Ibufenac; Ibuprofen; Ibuprofen Aluminum; Ibuprofen Piconol; Ilonidap; Indomethacin; Indomethacin Sodium; Indoprofen; Indoxole; Intrazole; Isoflupredone Acetate; Isoxepac; Isoxicam; Ketoprofen; Lofemizole Hydrochloride; Lomoxicam; Loteprednol Etabonate; Meclofenamate Sodium; Meclofenamic Acid; Meclorisone Dibutyrate; Mefenamic Acid; Mesalamine; Meseclazone; Mesterolone; Methandrostenolone; Methenolone; Methenolone Acetate; Methylprednisolone Suleptanate; Morniflumate; Nabumetone; Nandrolone; Naproxen; Naproxen Sodium; Naproxol; Nimazone; Olsalazine Sodium; Orgotein; Orpanoxin; Oxandrolane; Oxaprozin; Oxyphenbutazone; Oxymetholone; Paranyline Hydrochloride; Pentosan Polysulfate Sodium; Phenbutazone Sodium Glycerate; Pirfenidone; Piroxicam; Piroxicam Cinnamate; Piroxicam Olamine; Pirprofen; Prednazate; Prifelone; Prodolic Acid; Proquazone; Proxazole; Proxazole Citrate; Rimexolone; Romazarit; Salcolex; Salnacedin; Salsalate; Sanguinarium Chloride; Seclazone; Sermetacin; Stanozolol; Sudoxicam; Sulindac; Suprofen; Talmetacin; Talniflumate; Talosalate; Tebufelone; Tenidap; Tenidap Sodium; Tenoxicam; Tesicam; Tesimide; Testosterone; Testosterone Blends; Tetrydamine; Tiopinac; Tixocortol Pivalate; Tolmetin; Tolmetin Sodium; Triclonide; Triflumidate; Zidometacin; Zomepirac Sodium), or anti-histaminic agents (e.g. Ethanolamines (like diphenhydramine carbinoxamine), Ethylenediamine (like tripelennamine pyrilamine), Alkylamine (like chlorpheniramine, dexchlorpheniramine, brompheniramine, triprolidine), other anti-histamines like astemizole, theophyline, loratadine, fexofenadine, Bropheniramine, Clemastine, Acetaminophen, Pseudoephedrine, Triprolidine).

The compositions of present invention may be administered in a number of ways depending on whether local or systemic treatment is desired, and on the area to be treated. Administration may be topically (including ophthalmically, vaginally, rectally, intranasally), orally, by inhalation, or parenterally, for example by intravenous drip, subcutaneous, intraperitoneal or intramuscular injection. Injectables can be prepared in conventional forms, either as liquid solutions or suspensions, solid forms suitable for solution of suspension in liquid prior to injection, or as emulsions.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

However, since the compositions have particular application in the topical administration for a local effect, it is preferable that the composition is administered topically, which typically includes the delivery of the compositions to the skin, but may also include the delivery of the compositions into the nose and nasal passages through one or both of the nares. Suitable forms include ointments; lotions; creams; gels (e.g., poloxamer gel); drops; suppositories; sprays; liquids; powders; sprayable liquids; liquids that may be applied using a roll-on device; lacquers; and sustained release matrices of transdermal delivery devices such as patches. Administration of the compositions by inhalant can be through the nose or mouth via delivery by a spraying or droplet mechanism. Delivery can also be directly to any area of the respiratory system (e.g., lungs) via intubation. Conventional pharmaceutical carriers, aqueous, powder or oily bases, thickeners and the like may be necessary or desirable. The disclosed compositions can be administered, for example, in a microfiber, polymer (e.g., collagen), nanosphere, aerosol, lotion, cream, fabric, plastic, tissue engineered scaffold, matrix material, tablet, implanted container, powder, oil, resin, wound dressing, bead, microbead, slow release bead, capsule, injectables, intravenous drips, pump device, silicone implants, or any bio-engineered materials.

Also provided are materials comprising the herein provided. For example, provided are materials used to treat wounds, wherein the materials are coated with one or more helminthic parasite preparations. Non-limiting examples of materials used to treat wounds include bandages, steri-strip, sutures, staples, or grafts (e.g., skin grafts).

For example, the material (e.g., bandage, steri-strip, suture, staple, graft) can be soaked in the provided helminthic parasite preparations or a pharmaceutical compositions comprising helminthic parasite preparations at a concentration ranging from 10-200 µM. The material can then be dried and sealed in a sterile container. The material can also be immersed in liquid 10-30% pluronic gel at 4° C. containing one or more helminthic parasite preparations at 10-200 µM concentration. The material can then be brought to approximate room temperature so that the gel polymerizes, leaving a coat of parasite-impregnated gel surrounding the material, which can be sealed in a sterile container. The helminthic parasite preparation can also be incorporated into a cross-linkable hydrogel system, such as the poly(lactic-co-glycolic acid) (PLGA) or polyurethane, which can then be fashioned into materials for treating wounds (e.g., bandage, steri-strip, suture, staple, graft). Thus, provided are composite hydrogel-parasite materials.

Also disclosed are medical implants coated with the provided helminthic parasite preparation or compositions thereof before implantation in a subject. For example, a common problem in such implant surgeries is the formation of a contraction capsule around the implant from scar tissue formation that leads to undue hardening, contraction and ultimately misshaping of the tissue of interest. The use of the present helminthic parasite preparations in or on the implant can reduce or prevent this misshaping. Non-limiting examples of medical implants include: limb prostheses, breast implants, penile implants, testicular implants, artificial eyes, facial implants, artificial joints, heart valve prostheses, vascular prostheses, dental prostheses, facial prosthesis, tilted disc valve, caged ball valve, ear prosthesis, nose prosthesis, pacemakers, cochlear implants, and skin substitutes (e.g., porcine heterograft/pigskin, BIOBRANE, cultured keratinocytes).

Provided herein is a method of promoting wound healing following tissue injury in a subject, comprising administering to the subject one or more of the herein provided compositions (e.g., helminthic parasite preparation) in a pharmaceutically acceptable carrier. Further provided is a method of treating a subject with tissue injury, comprising administering to the subject one or more of the herein provided compositions in a pharmaceutically acceptable carrier.

"Promote," "promotion," and "promoting" refer to an increase in an activity, response, condition, disease, or other biological parameter. This can include but is not limited to the initiation of the activity, response, condition, or disease. This may also include, for example, a 10% increase in the activity, response, condition, or disease as compared to the native or control level. Thus, the increase can be a 10, 20, 30, 40, 50, 60, 70, 80, 90, 100%, or any amount of increase in between as compared to native or control levels.

By "treat" or "treatment" is meant a method of reducing the effects of a disease or condition. Treatment can also refer to a method of reducing the underlying cause of the disease or condition itself rather than just the symptoms. The treatment can be any reduction from native levels and can be but is not limited to the complete ablation of the disease, condition, or the symptoms of the disease or condition. For example, a disclosed method for promoting wound healing is considered to be a treatment if there is a 10% reduction in one or more symptoms of the disease in a subject with the disease when compared to native levels in the same subject or control subjects. Thus, the reduction can be a 10, 20, 30, 40, 50, 60, 70, 80, 90, 100%, or any amount of reduction in between as compared to native or control levels.

As used herein, "subject" includes, but is not limited to, a vertebrate, and more specifically a mammal (e.g., a human, horse, pig, rabbit, dog, sheep, goat, non-human primate, cow, cat, guinea pig or rodent), a fish, a bird or a reptile or an amphibian. The term does not denote a particular age or sex. Thus, adult and newborn subjects, as well as fetuses, whether male or female, are intended to be covered. A patient refers to a subject afflicted with a disease or disorder. The term "patient" includes human and veterinary subjects.

The provided method can reduce scar tissue formation in a subject following tissue injury. By "scar tissue" is meant the fibrous (fibrotic) connective tissue that forms at the site of injury or disease in any tissue of the body, caused by the overproduction of disorganized collagen and other connective tissue proteins, which acts to patch the break in the tissue. Scar tissue may replace injured skin and underlying muscle, damaged heart muscle, or diseased areas of internal organs such as the liver. Dense and thick, it is usually paler than the surrounding tissue because it is poorly supplied with blood, and although it structurally replaces destroyed tissue, it cannot perform the functions of the missing tissue. It is composed of collagenous fibers, which will often restrict normal elasticity in the tissue involved. Scar tissue may therefore limit the range of muscle movement or prevent proper circulation of fluids when affecting the lymphatic or circulatory system. Glial scar tissue following injury to the brain or spinal chord is one of the main obstacles to restoration of neural function following damage to the central nervous system. A reduction in scar tissue can be assessed by the population of cell types within the injured site. For example, a reduction in glial scar tissue can be estimated by an increased ratio of neuronal to astrocytic cells. A reduction in scar tissue formation can be measured by a simple measurement of scar width or area of scar tissue (Wilgus et al., 2003). In addition histological assessments can be made about the restoration of structural complexity within healed tissue in comparison to normal tissue.

In addition to reducing fibrotic tissue formation in a subject in following tissue injury, the provided compositions and methods can also be used to treat disorders associated with pathological increases in fibrotic tissue formation in a subject, such as for example, psoriasis, cutaneous and systemic mastocytosis, asthma, eczema, sinusitis, atherosclerosis, rheumatoid arthritis, inflammatory bowel disease, multiple sclerosis, pulmonary fibrosis and cystic fibrosis. A reduction in fibrotic tissue formation in a subject can be measured by clinical judgment of a doctor assessing whether a regain in normal structure and function of a given tissue and/or organ in a subject has resulted following a treatment. As an example, for psoriasis a doctor would assess the subject's skin to determine whether there has been a reduction in patches of raised red skin covered by flaky white buildup. Certain kinds of psoriasis, are characterized by a pimple-ish (pustular psoriasis) or burned (erythrodermic) appearance. In such cases, the doctor would determine whether treatment has resulted in the reduction of these symptoms. In the case of an tissue or organ in which a subject where a doctor judges that a biopsy is clinically available and/or necessary or in an animal model of the human disease, tissue fragments of bioposies would be prepared and tissue histological structure would be assessed by a clinical pathologist and/or trained histopathologist to determine if reduction in fibrosis and restoration of normal tissue structure and function has occurred. The area of fibrosis to normal tissue could also be quantitatively assessed on such histological preparations.

The provided method can restore normal tissue mechanical properties such as tensile strength following tissue injury in a subject. "Tensile strength" refers to the amount of stress or strain required to break the tissue or wound. The tensile strength of treated wounds can be 60, 65, 70, 75, 80, 85, 90, 95, 100% that of uninjured tissue within 3 months after treatment. Thus, provided is a method of restoring tissue mechanical properties, including increasing tensile strength of a healed injury to approach or reach that of normal uninjured tissue, in a subject comprising administering to the subject one or more of the herein provided compositions (e.g., polypeptides, nucleic acids, or vectors) in a pharmaceutically acceptable carrier.

The provided method can improve tissue regeneration following tissue injury in a subject. By "regeneration" is meant the renewal, re-growth, or restoration of a body or a bodily part, tissue, or substance after injury or as a normal bodily process. In contrast to scarring, tissue regeneration involves the restoration of the tissue to its original structural, functional, and physiological condition. This is also referred to herein as tissue "complexity". The restoration can be partial or complete, meaning 10, 20, 30, 40, 50, 60, 70, 80, 90, 100% restoration, or any amount of restoration in between as compared to native or control levels. As an example, in the case of a skin injury, tissue regeneration can involve the restoration of hair follicles, glandular structures, blood vessels, muscle, or fat. In the case of a brain injury, tissue regeneration can involve maintenance or restoration of neurons. As an example in the case of skin an improvement in tissue regeneration can be assessed by measurements of the volume of fibrous scar tissue to normal regenerated skin as a ratio. As another example, counts can be made of discrete regenerating structures such as regenerating skin glands normalized to the volume of the wound area.

In one aspect, tissue regeneration involves the recruitment and differentiation of stem cells to replace the damaged cells. As used herein, a "stem cell" is an undifferentiated cell found among differentiated cells in a tissue or organ, or introduced from an external source for e.g., Embryonic stem cells, Adult Bone Marrow stem cells, that can renew itself and differentiate to yield the major specialized cell types of the tissue or organ. The primary roles of stem cells in a living organism are to maintain and repair the tissue in which they are found. By stem cell differentiation is meant the process whereby an unspecialized cell (e.g., stem cell) acquires the features of a specialized cell such as a skin, neural, heart, liver, or muscle cell. As an example, in the case of a skin injury, tissue regeneration can involve the differentiation of stem cells present in the epithelium into hair follicles (Alonso and Fuchs, 2003). In the case of a brain injury, tissue regeneration can involve the differentiation of stem cells into neurons. The provided method can enhance stem cell differentiation following tissue injury in a subject. Enhanced stem cell differentiation can be measured by providing a clinically acceptable genetic or other means of marking endogenous or engrafted stem cells and determining the frequency of differentiation and incorporation of marked stem cells into normal tissue structures. As another example, certain structures such as hair follicles are known to be regenerated from endogenous stem cells following tissue injury. As such, counts of hair follicles normalized to tissue injury area would serve as a quantitative assessment of enhanced stem cell differentiation.

The provided method can reduce inflammation in a subject. By "inflammation", "inflammatory response" or "immune response" is meant the reaction of living tissues to injury, infection or irritation characterized by redness, warmth, swelling, pain, and loss of function, produced as the result of increased blood flow and an influx of immune cells and secretions. Inflammation is the body's reaction to invading infectious microorganisms and results in an increase in blood flow to the affected area, the release of chemicals that draw white blood cells, an increased flow of plasma, and the arrival of monocytes (or astrocytes in the case of the brain) to clean up the debris. Anything that stimulates the inflammatory response is said to be inflammatory. Thus, in addition to reducing inflammation in a subject in response to tissue injury, the provided compositions and methods can also be used to treat disorders associated with pathological increases in levels of inflammatory cells, including, for example, asthma, eczema, sinusitis, atherosclerosis, rheumatoid arthritis, inflammatory bowel disease, cutaneous and systemic mastocytosis, psoriasis, and multiple sclerosis. Treatment with the provided polypeptide can also reduce itching, for example of healing wounds. Generally, itching results from histamine release by mast cells. The provided polypeptide can reduce mast cell degranulation and histamine release. Thus, the provided polypeptide can be used to treat conditions involving histamine release, including, but not limited to, itching, scratching, sinus irritation, allergic cough, red eyes, asthma, and eczema.

A reduction in inflammation can be measured by a reduction in the density of inflammatory cell types such as, for example, monocytes or astrocytes. A reduction in inflammation can be measured by a reduction in the density of inflammatory cell types such as, for example, neutrophils, mast cells, basophils, and monocytes. A reduction in inflammation can be calculated by an in vivo measurement of neutrophil activity (Jones et al., 1994). In addition factors like frequency of mast cell degranulation or measurement of histamine levels or levels of reactive oxygen species can be used as measurements of reduction in inflammation. The level of inflammation can also be indirectly measured by checking for transcription levels of certain genes by qRT-PCR for e.g. genes like, Interferon-alpha, -beta and -gamma, Tumor Necrosis Factor-alpha, Interleukine 1 beta, -2, -4, -5, -6, -8, -12, -18, -23, -27, CD4, CD28, CD80, CD86, MHCII, and iNOS. Measurement of pro-inflammatory cytokine levels in the tissues and or bodily fluids of the subject including plasma can measure a reduction in inflammation. It is noteworthy that a mechanism of ACT peptide action may be by inhibition of inflammatory cell migration and/or inhibition of pro-inflammatory chemicals (histamine, reactive oxygen species) and pro-inflammatory cytokines such as Interleukin (IL)-1, IL-6, IL-8 and tumor necrosis factor (TNF).

As used herein, tissue injury can result from, for example, a scrape, cut, laceration wound, crush wound, compression wound, stretch injury, bite wound, graze, bullet wound, explosion injury, body piercing, stab wound, burn wound, wind burn, sun burn, chemical burn, surgical wound, surgical intervention, medical intervention, host rejection following cell, tissue or organ grafting, pharmaceutical effect, pharmaceutical side-effect, bed sore, radiation injury, cosmetic skin wound, internal organ injury, disease process (e.g., asthma, cancer), infection, infectious agent, developmental process, maturational process (e.g., acne), genetic abnormality, developmental abnormality, environmental toxin, allergen, scalp injury, facial injury, jaw injury, foot injury, toe injury, finger injury, bone injury, sex organ injury, joint injury, excretory organ injury, eye injury, corneal injury, muscle injury, adipose tissue injury, lung injury, airway injury, hernia, anus injury, piles, ear injury, retinal injury, skin injury, abdominal injury, arm injury, leg injury, athletic injury, back injury, birth injury, premature birth injury, toxic bite, sting, tendon injury, ligament injury, heart injury, heart valve injury, vascular system injury, cartilage injury, lymphatic system injury, craniocerebral trauma, dislocation, esophageal perforation, fistula, nail injury, foreign body, fracture, frostbite, hand injury, heat stress disorder, laceration, neck injury, self mutilation, shock, traumatic soft tissue injury, spinal cord injury, spinal injury, sprain, strain, tendon injury, ligament injury, cartilage injury, thoracic injury, tooth injury, trauma, nervous system injury, aging, aneurism, stroke, digestive tract injury, infarct, or ischemic injury.

The materials described above as well as other materials can be packaged together in any suitable combination as a kit useful for performing, or aiding in the performance of the disclosed method. It is useful if the kit components in a given kit are designed and adapted for use together in the disclosed method. For example disclosed are kits for promoting wound healing, the kit comprising one or more of the helminthic parasite preparations provided herein in a pharmaceutically acceptable carrier. Such kits can also include gels, bandages, Millipore tapes, Medicated Q-tips, Sprays, props, Syrups, Liquids, Disposable tubes or pouches. The kits also can contain instructions for proper use and safety information of the product or formulation. The kits may contain dosage information based on the application and method of administration as determined by a doctor.

In some embodiments, the present invention is also directed to a method of treating an acute lung injury by administering to a patient in need of treatment one or more helminthic parasite preparations, preferably live, or an active mimic thereof, where the NES product is being preferred.

EXAMPLES

Example 1

Figure 3:
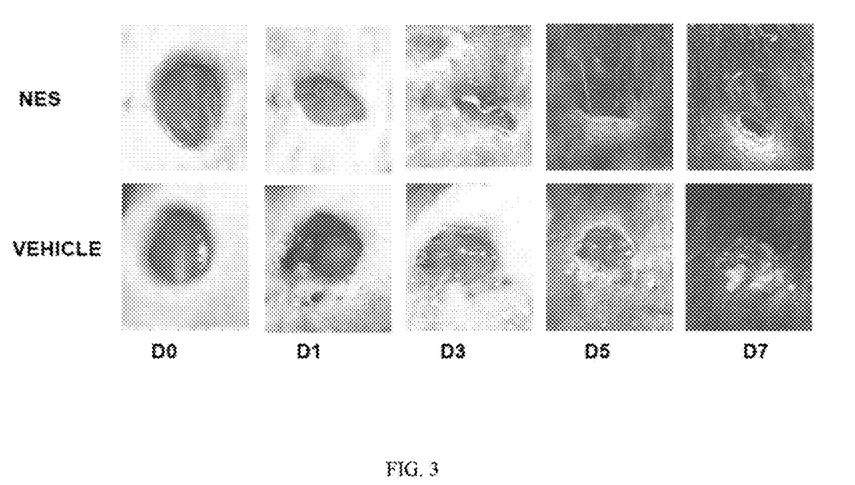
FIG. 3 are representative image of punch biopsies from untreated (control; vehicle) mice and mice treated with NES at different time points.

To examine whether helminthes accelerate cutaneous wound healing, punch biopsies were used to create defined cutaneous wounds in mice based on a protocol previously described (Chigurupati, S., et al. *PLoS One* 5, e10044 (2010); Reiss, M. J., et al. *Surgery* 147, 295-302 (2010); Syeda, M. M., et al. *Am J Pathol* 181, 334-346 (2012); Ojha, N., et al. *Free Radic Biol Med* 44, 682-691 (2008); incorporated herein by reference in their entirety). Specifically, C57BL.6 male mice, age 8-10 weeks, were used for this model experiment. The backs of the mice were shaved with standard animal hair clippers and disinfected with betadine (Fisher, N.J., USA). After 48 hours, mice were infected either with 500 *Nippostrongylus brasiliensis* (Nb) third-stage larvae (L3) or left untreated (control). 24 hours after the Nb infection, 50 microgram of NES product derived from both Nb L3 larvae and Nb L5 adult worms were injected subcutaneously at the site of wounding. Forty-eight hours after Nb inoculation, using microdissecting forceps (Roboz, Inc., MD, USA), the skin of the animal was lifted and a 5-mm dermal biopsy punch (Acuderm Inc, Fl, USA) was administered through the skin. Seventy-two hours after wounding another dose of 50 micrograms NES derived from 1.3 larvae and L5 adult worms was applied over the wound. As shown in FIG. 3, the wound closure was monitored over a 9 day period by digital photography and wound area (pixels$^2$) was quantitated from photographs using an Axio-vision 4.8.1 (Carl Zeiss AG, Germany) in a blinded manner.

Example 2

In order to assess the potential of parasite and parasite derived products, NES was collected form L3 and L5 larvae, concentrated (as described in Ojha, 2008), and analyzed for contaminating endotoxin present in the NES by using an endpoint chromomeric Limulus amebocyte lysate assay (QCL-1000; Lonza, Walkersville, Md.). The LPS levels of NES products were found to be less than 3 units 1 ml of NES preparation. Mice were infected with 300 L3 and administered NES subcutaneously 24 later. Forty-eight hours post infection 5 mm punch biopsies were administered to either naïve mice or mice treated with Nb+NES. Three days after wounding, 50 micrograms of NES was applied over the wound. Wound closure was assessed over a period of 9 days and digital photographs of wound closure taken. Using digital imaging analysis, the area of the wound was quantitated in controls and in mice administered Nb+NES. As shown in FIG. 2A, a statistically significant enhanced wound closure was found to occur in biopsies from mice administered Nb+NES compared to untreated control biopsies. Statistical significance was observed from day 6 to day 9 after punch biopsy. Taken together these data suggest accelerated wound healing occurs following administration of Nb+NES.

Example 3

An experimental in vivo wound healing experiments shown in Examples 1 and 2 has been repeated with NES alone. Specifically. NES was subcutaneously injected at the site of punch biopsy 24 hours before treatment. NES was then administered via subcutaneous injection every 24 hours thereafter. Biopsies were photographed on a daily basis and the wound area quantitated as previously described. In these studies, a dose response experiment reveals that administration of NES alone is sufficient to accelerate wound closure as shown in FIG. 2B.

Tissues were collected at specific timepoints and assess through immunohistological techniques changes in inflammatory cells, the degree of fibrosis, reepithelialization, angiogenesis, and tissue granulation. Tissues were also collected to examine changes in gene expression with a particular focus on genes associated with wound healing and the helminth-induced type 2 immune response including: specific Th1 and Th2 cytokines, collagens, collegenases, IGF-1, Arg1, VEGF, FGF, and RELMα.

Example 4

NES is administered immediately after punch biopsy to determine whether administration of NES can affect established wounds. Without being bound by theory it is believed that NES accelerates healing of established wounds and accelerate healing of acute and chronic wounds.

Example 5

NES and Nb infection are administered immediately after punch biopsy to determine whether administration of NES can affect established wounds. NES and Nb infection accelerate healing of established wounds. This treatment accelerates healing of acute and chronic wounds.

Another important experimental model addresses chronic wound healing where wounding is made in the ear. NES is administered immediately after a wound is inflicted. NES accelerates healing of chronic wounds.

Finally, the pig is an experimental model generally considered most similar to humans with regard to wound healing. A convincing preclinical experiment is the efficacy of our preparation is tested in a pig wound healing model. Additional studies examine the efficacy of wound healing enhancement in a type 1 diabetes experimental model, the NOD mouse.

It will be appreciated by persons skilled in the art that the present invention is not limited to what has been particularly shown and described. Rather, the scope of the present invention is defined by the claims which follow. It should further be understood that the above description is only representative of illustrative examples of embodiments. The description has not attempted to exhaustively enumerate all possible variations. The alternate embodiments may not have been presented for a specific portion of the invention, and may result from a different combination of described portions, or that other un-described alternate embodiments may be available for a portion, is not to be considered a disclaimer of those alternate embodiments. It will be appreciated that many of those un-described embodiments are within the literal scope of the following claims, and others are equivalent. Furthermore, all references, publications, U.S. Patents, and U.S. Patent Application Publications cited throughout this specification are hereby incorporated by reference as if fully set forth in this specification.

The invention claimed is:

1. A method of accelerating wound healing in a patient having a wound inflicted on the skin, comprising:

i. identifying the patient having the wound inflicted on the skin, and ii. administering to said patient a helminthic parasite preparation consisting essentially of excretory/secretory (ES) product and at least one pharmaceutically acceptable carrier or excipient, wherein the wound inflicted on the skin comprises one of eczema, psoriasis, and cutaneous mastocytosis, and wherein the excretory/secretory (ES) product is excretory/secretory (ES) product or an immune triggering portion thereof of *Nippostronglyus brasiliensis* (Nb).

2. The method of claim 1, wherein the administration is topical.

3. The method of claim 1, wherein the administration occurs by subcutaneous injection.

4. The method of claim 1, wherein the administering step occurs more than once.

5. A method of accelerated wound healing in a patient having an open wound on the skin, comprising:
i. identifying the patient having the open wound inflicted on the skin, and ii. administering to said patient a helminthic parasite preparation consisting essentially of excretory/secretory (ES) product and a pharmaceutically acceptable carrier or excipient, wherein the administering is repeated beyond a point at which the wound is closed.

6. The method of claim 5, wherein the method further comprises tissue regeneration in the patient having the wound inflicted on the skin.

7. The method of claim 6, wherein the tissue regeneration comprises restoration of hair follicles, glandular structures, blood vessels, muscle, or fat.

8. The method of claim 5, wherein the administration is topical.

9. The method of claim 5, wherein the administration occurs by subcutaneous injection.

10. The method of claim 5, wherein the excretory/secretory (ES) product is excretory/secretory (ES) product or an immune triggering portion thereof of *Nippostronglyus brasiliensis* (Nb).

* * * * *